(12) United States Patent  
Bastide et al.

(10) Patent No.: US 10,650,918 B2  
(45) Date of Patent: May 12, 2020

(54) CROWDSOURCING HEALTH IMPROVEMENTS ROUTES

(71) Applicant: INTERNATIONAL BUSINESS MACHINES CORPORATION, Armonk, NY (US)

(72) Inventors: Paul R. Bastide, Boxford, MA (US); Isabell Filiz Kiral-Kornek, Collingwood (AU); Dwarikanath Mahapatra, Melbourne (AU); Susmita Saha, Melbourne (AU); Arun Vishwanath, Blackburn (AU); Stefan Von Cavallar, Sandringham (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 240 days.

(21) Appl. No.: 15/611,519

(22) Filed: Jun. 1, 2017

(65) Prior Publication Data

US 2018/0349563 A1   Dec. 6, 2018

(51) Int. Cl.
*G09B 29/00* (2006.01)
*G16H 10/60* (2018.01)
*G16H 50/70* (2018.01)
*G16H 20/30* (2018.01)

(52) U.S. Cl.
CPC ............ *G16H 10/60* (2018.01); *G16H 20/30* (2018.01); *G16H 50/70* (2018.01)

(58) Field of Classification Search
CPC .................................. G16H 10/60; G16H 20/30
See application file for complete search history.

(56) References Cited

U.S. PATENT DOCUMENTS

| | | | |
|---|---|---|---|
| 7,251,454 B2 | 7/2007 | White | |
| 2010/0205060 A1 | 8/2010 | Athsani et al. | |
| 2012/0015779 A1 | 1/2012 | Powch et al. | |
| 2012/0116550 A1 | 5/2012 | Hoffman et al. | |
| 2014/0303892 A1* | 10/2014 | Morlock | G01C 21/20 701/533 |
| 2015/0081210 A1* | 3/2015 | Yeh | G06F 16/60 701/428 |
| 2015/0142689 A1* | 5/2015 | Squires | G06Q 30/0279 705/329 |

(Continued)

OTHER PUBLICATIONS

Emrich et al. "Personalized And Situation-Aware Recommendations For Runners." PACIS. 2011.

(Continued)

*Primary Examiner* — Jess Whittington
(74) *Attorney, Agent, or Firm* — F. Chau & Associates, LLC (57) ABSTRACT

A computer-implemented method for determining routes includes receiving a user's location and health measures, for a plurality of users, analyzing the plurality of users and their corresponding locations to determine health behaviors at a given location and time, receiving a request from a user for a route, developing a route to the user's destination from a current location to obtain a target health behavior within a given threshold or constraint based on the plurality of user's healthy behaviors, and presenting the route on a computing device.

28 Claims, 6 Drawing Sheets

(56) References Cited

U.S. PATENT DOCUMENTS

2017/0153119 A1* 6/2017 Nieminen ............ G01C 21/343

OTHER PUBLICATIONS

Kranz et al. "The mobile fitness coach: Towards individualized skill assessment using personalized mobile devices." Pervasive and Mobile Computing 9.2 (2013): 203-215.

Vikstrom, "Location-aware mobile fitness coaches Current applications and future possibilities." Umea's 13th Student Conference in Computer Science. 2009.

Mapometer.com.

http://www.suunto.com/en-AU/Worlds/Training-World/Discover-new-routes/.

http://www.guardiantechnologies.com/healthy-living/health-risks-of-inactivity/.

http://www.hopkinsmedicine.org/healthlibrary/conditions/cardiovascular_diseases/risks_of_physical_inactivity_85, P00218/.

http://trailrunnerx.com/en_about/.

http://www.mapmyride.com/app/.

* cited by examiner

CROWDSOURCING HEALTH IMPROVEMENTS ROUTES

BACKGROUND

Technical Field

Embodiments of the disclosure are directed to determining exercise routes based on crowdsourcing.

Discussion of the Related Art

The lack of physical activity is known to be a risk factor for cardiovascular disease, high blood pressure, certain cancers, self-esteem and other diseases. Further, inactivity related to age, work and lifestyle are additional factors.

Many map applications determine a route for a user based on efficiency, such as a shortest time, a shortest distance, safety, or avoiding toll roads. These routing applications minimize activity, and ignore an opportunity to enhance a user's health.

For example, one route planner for sports people enables people to map runs, cycles and walks and calculate the distances and elevation profiles of routes. It also provides training logs to track progress and monitor the calories burned. This application can be used by athletes as a tool to train for marathons, half-marathons and triathlons and charity runs. However, it requires a user to explicitly select a route, and presents corresponding estimates for the calories consumed.

SUMMARY

According to an embodiment of the disclosure, there is provided a computer-implemented method for determining routes, including receiving a user's location and health measures, for a plurality of users, analyzing the plurality of users and their corresponding locations to determine health behaviors at a given location and time, receiving a request from a user for a route, developing a route to the user's destination from a current location to obtain a target health behavior within a given threshold or constraint based on the plurality of user's healthy behaviors, and presenting the a route on a computing device.

According to a further embodiment of the disclosure, the method includes joining the location and health measures data together into a single data element based on time According to a further embodiment of the disclosure, the health behavior includes one or more of a number of calories, a number of steps, and at least a health measure.

According to a further embodiment of the disclosure, the route is presented as a map on the computing device.

According to a further embodiment of the disclosure, location data includes a user's location based on GPS data and cell triangulation, a user's elevation, terrain, and environmental attributes, a user's health measures include activity, blood pressure, speed, ailments, heartrate, calories burned, and the data is stamped with a time and date.

According to a further embodiment of the disclosure, analyzing the plurality of users and their corresponding locations comprises aggregating biometric data and route data over a population of users in a data cloud for a given user and normalizing data over a distance for data values over a predetermined threshold.

According to a further embodiment of the disclosure, the method includes creating an aggregated heatmap that represents health, geographical, and topographical data as part of the map.

According to a further embodiment of the disclosure, developing a route to the user's destination comprises using a metric along with a graph traversal algorithm to select a route that increases health related values while minimizing the overall difference in the route assigned to a user.

According to a further embodiment of the disclosure, a metric includes one or more of a number of calories, a number of vertical steps, number of horizontal steps, increase in beats per minute, a distance, and mode of transportation.

According to a further embodiment of the disclosure, the method includes presenting a variety of route options to a user, and receiving a user's choice selected from the variety of route options.

According to a further embodiment of the disclosure, the method includes creating a map that highlights opportunities to burn extra calories or change to healthier habits.

According to a further embodiment of the disclosure, the method includes normalizing map regions without enough data with similar data based on elevation, distance and pitch.

According to a further embodiment of the disclosure, the method includes creating an aggregated heatmap that represents health, geographical, and topographical elements for the plurality of users.

According to a further embodiment of the disclosure, the method includes creating an aggregated heatmap based on the similarity of the user to a select cohort of the plurality of users.

According to another embodiment of the disclosure, there is provided a non-transitory program storage device readable by a computer, tangibly embodying a program of instructions executed by the computer to perform the method steps for determining exercise routes.

DETAILED DESCRIPTION OF EXEMPLARY EMBODIMENTS

Exemplary embodiments of the disclosure as described herein generally provide systems and methods for determining exercise routes based on crowdsourcing. While embodiments are susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

Embodiments of the disclosure use crowdsourcing to determine health improvements routes, by recording location, time, date and health measures, such as activity, blood pressure, speed, ailments, heart rate, calories burned, etc., for users by analyzing a crowd, i.e., a population of users, and their corresponding locations to determine health behaviors in a given location/time to route a given user to a destination based on the crowds healthy behaviors/activity. Embodiments of the disclosure can help change an inactive lifestyle into an active lifestyle through routing, which can be done every day.

Crowdsourcing is desirable for the following reasons.

(1) To corroborate that the measurements recorded by a user's fitness device are in fact accurate, and that there are no anomalies. For example, if an activity tracking device shows that a particular track leads to 200 calories being burnt, how does a user know that this is accurate and that the device measurements are not drifting? Crowdsourcing can help mitigate this risk by using data from a large number of users with health/fitness condition similar to the individual to corroborate the measurement statistics, such as the average number of calories burnt when a particular track is chosen, etc.

(2) When a user is at a new location, i.e. does not have tracks recorded and stored for that location, crowdsourcing information can suggest tracks closest to the user's own personal preferences and health goals. For example, mapping topographical information related to a new mountain range and goals to meet. Although this geography has not been previously explored, a crowdsourced system can create a heat-map from known geographies and overlay a path that is closest to the one that is desirable.

(3) To suggest/reflect changes in routes dynamically to the user. For example, a pre-recorded track may not be suitable to run at a particular moment for a variety of reasons, such as too much pollen in the region to which the user is allergic, bad/inclement weather which causes a slippery track, epidemic/flu outbreak in a region, fallen trees causing disruptions, construction activity, etc.

Exemplary embodiments of the disclosure can suggest routes to a user that are personalized to the user and his/her current health condition, with a focus on health/fitness. For example, a user could query the system for the following information: "I have 20 minutes and my goal is to burn 200 calories. Suggest a route." Or: "I have 20 minutes and my goal is to burn 200 calories. Suggest a route that combines both riding and running". Or: "I have 20 minutes and my goal is to burn 200 calories. Suggest a route that involves running along the river", etc.

Alternatively, a user could pose the following query: "Suggest a route in which I could maintain a heart rate of around 150 bpm for 5 minutes while running", or "Suggest a route in which I could maintain a heart rate of around 150 bpm for 5 minutes running, then 80 bpm walking on an incline of say 30 degrees for 15 minutes", etc.

Embodiments of the disclosure can correlate the calories burned by a group of people traveling over a given distance, such as the length of a block, one meter, one kilometer, etc., along a path to gather an average, and to put the burned calories together to get the user to a destination based on greedily working towards a goal. The output of an embodiment of the disclosure is a map displayed on a computing device or directions for determining a route provided to the computing device.

Figure 1:
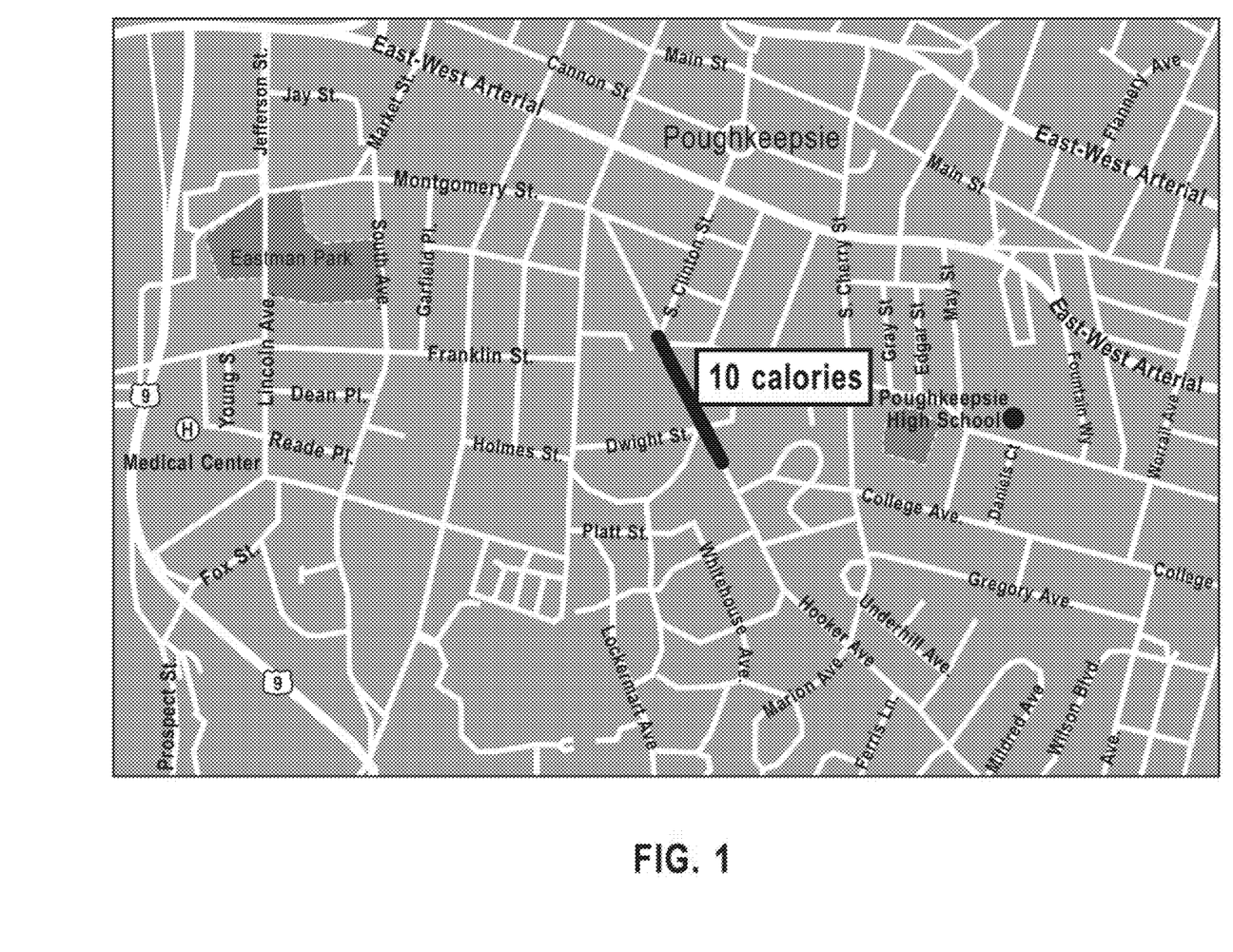
FIG. 1 is a map that highlights a route along a public street and indicates the number of calories burned along that route.
Figure 2:
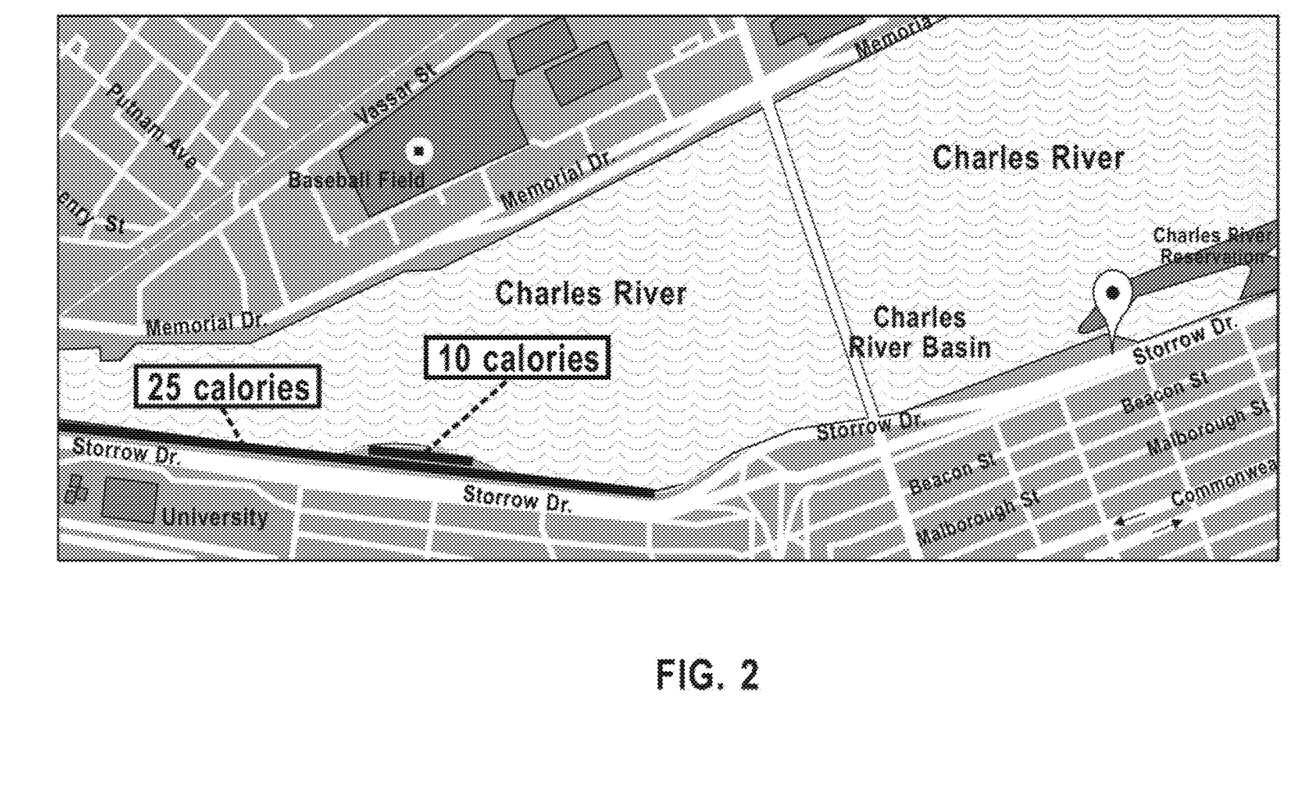
FIG. 2 is another map that indicates where differing amounts of calories were burned along another route

A scenario according to an embodiment involves crowdsourcing health data. Let Bob be a user of a wearable device, and suppose Bob has recorded his weight and his height in the devices corresponding smartphone application. Bob's device is paired with his phone and continually monitors his heart rate and his location. Bob's device application synchronizes the data with the device's data cloud. An embodiment of the disclosure can retrieve the data for health and Bob's location and infers the calories burned in a given location or over a limited distance, such as 100 meters, and show it on a map displayed on the user's computing device. For example, FIG. 1 is a map that highlights a route along a public street and indicates that 10 calories were burned along that route. Alternatively, Bob may have run on along a particular street a few times, and the average calories burned at this location can be overlayed at a granular level by an embodiment of the disclosure. For example, FIG. 2 is another map that indicates where differing amounts of calories (25 calories and 10 calories in the map) were burned along another route.

Figure 3A:
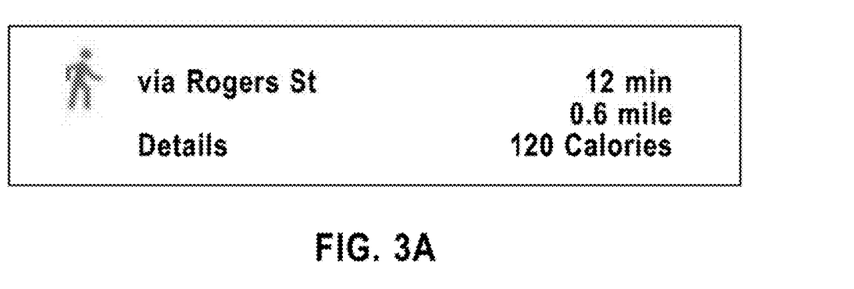
FIG. 3A illustrates an exemplary output of an embodiment of the disclosure.
Figure 3B:
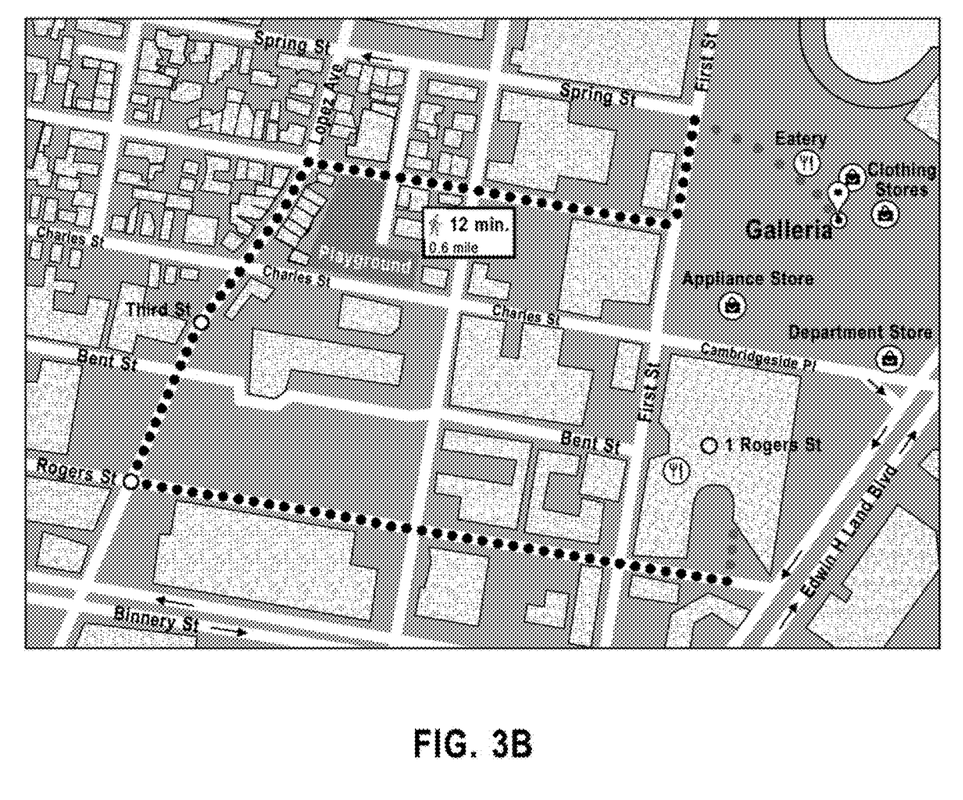
FIG. 3B shows a mapping solution displayed on a computing device according to an embodiment of the disclosure.

Another scenario according to an embodiment involves routing. Let Alice be a user of a wearable device, and suppose Alice has recorded her weight and her height in the device's smartphone application. In addition suppose Alice has also recorded her target goals: burn 2200 calories a day. When Alice opens her maps application, an embodiment of the disclosure can detect that Alice is 1000 calories below her goal, and behind her pace. Referring now to FIGS. 3A and 3B, Alice can enter a destination, such as a store in a shopping mall, and her current location, such as the address of an office building on Rogers Street, and an embodiment can greedily route Alice based on the calories to be burned. FIG. 3A illustrates an exemplary output of an embodiment of the disclosure, which indicates that a 0.6 mile route along Rogers Street will take 12 minutes and burn 120 calories. After Alice confirms, a mapping solution according to an embodiment is displayed on her computing device, as shown in FIG. 3B by the dotted line 31 from her initial location 30 to her destination 32, and begins routing Alice based on calories obtained.

Figure 4:
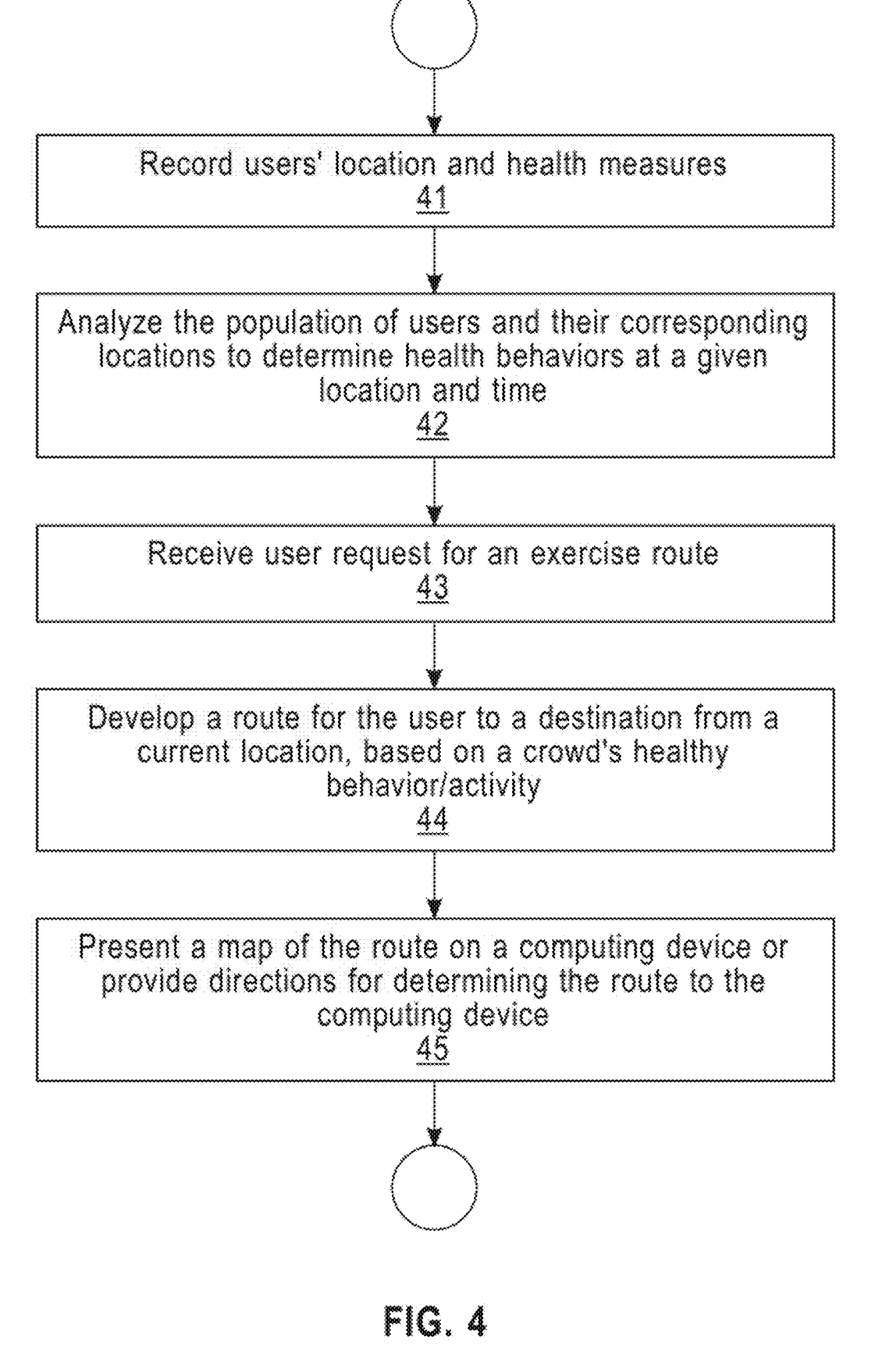
FIG. 4 is a flowchart of a method according to embodiments of the disclosure.

Methods according to embodiments of the disclosure include the following steps, with reference to the flowchart of FIG. 4. Referring now to the figure, a first step 41 is to record users' location and health measures. Embodiments of the disclosure can obtain access to the crowdsourced data by continuously recording user's heartrate/biometric data over a travel route. Embodiments of the disclosure record location and health measures, such as: location, based on GPS data and cell triangulation; elevation; metadata, such as time and date; health measurements, such as activity, blood pressure, speed, ailments, heart rate, calories burned; terrain, such as mud or grass, etc.; and environmental attributes, such as temperature, humidity, etc. The location is recorded along with the health measurements, and the data is joined together into a single data element based on time, e.g., {"HR": 85, "X": 1, "Y": 2, "DATE": "03MAR2016" }, where "HR" is a heartrate, "X" and "Y" may a longitude and latitude or X-Y positions on a grid, and "DATE" is the date. Each joined data element is limited to a single user. The user's personal identifiable information need not be stored or saved along with the data.

Embodiments of the disclosure can limit the exposure of private locations and personal data based on the number of sourced or unique individuals reporting data in a given area. For example, 15 people may be needed to report before the data is used in the analysis of health routes. The data is stored with other crowd-sourced routing, measures and location data.

A next step 42 is to analyze the population of users and their corresponding locations to determine health behaviors at a given location and time. Embodiments of the disclosure can aggregate over a population of users in a data cloud for a given user. The data being aggregated includes biometric data and route data as correlated by GPS or location positioning. Embodiments of the disclosure can also normalize over a distance for data values over a threshold, e.g., 85 BPM over a 100 meter arc, for a given user. For example if a current heart rate reading is 170 bpm, and if after moving 10 feet it reads 120 bpm, there may be some inaccuracy. The user may have gone up a set of stairs quickly. Therefore normalizing the beats per minute over a distance traveled is more accurate. Sampling multiple times over a long period of time and applying statistics yields a better result, while sampling over short periods of time will likely yield inaccurate data. The normalized arc/location provides an average effect over a given distance for a person, rather than weighting a high degree of sampling. The arc distance can be changed based on location, e.g., a train station may be smaller as people move less frequently than a running track.

According to embodiments, upon receiving a request from a user for an exercise route at step 43, another step 44 is developing a route for the user to a destination from a current location based on a crowd's healthy behaviors/activity. Embodiments of the disclosure can detect the target health behavior, such as the number of calories, and greedily develops a route to obtain a target health behavior within a given threshold or constraint. Embodiments of the disclosure develop a route by using a metric/value along with any well know graph/traversal algorithm to select a route that offers the best change. Examples of a metric/value according to an embodiment include calories, number of vertical steps, number of horizontal steps, increase in bpm, etc. A best change according to an embodiment is a change that increases other health related values while minimizing the overall difference in the route assigned to a user.

According to embodiment, a route can be determined to maximize a number of calories or a distance. For example, if a user is sent along the Boston Marathon route, the user may get to burn 10K calories walking to and from work. If a route deflects only a certain number of calories, a user can get where they are going while managing to burn the most calories, potentially regardless of time. A route can be determined based on a longer route home and a potential to reduce heart rate. Embodiments can route based on different modes of transportation or conveyance, such as walking by a river, running by the river, shaded running away from the rain on the river. Alternatively, an aggregated heatmap can be created that represents the crowdsourced health, geographical, and topographical elements, and the aggregated information can be presented as part of the map. Embodiments can present a heatmap that shows various starting points/routes in an immediate vicinity of the starting points. The heatmap can show various routes between start and destination.

One a route has been determined, a final step 45 according to an embodiment is presenting a route to the user. The route can be presented as a map of the route on a computing device or by providing directions for determining the route to the computing device.

Further embodiments of the disclosure can filter based on personal attributes, e.g., the person is a male aged 18-35 years and likes sports radio, and can create a map that highlight the opportunities to burn extra calories or change to healthier habits. Embodiments can normalize areas without enough data with similar data based on elevation, distance and pitch (i.e. incline or grade). Embodiments can present a variety of options/routes for the user, so that they can choose the best path for him/her.

Each calculated route option should take into consideration these components to determine the most appropriate path/route to the destination and which fulfils the users' goals. In one embodiment, an approach to determining the differences and thus the routing options can be performed by simple rule-based approach. For example, if an area around a user and their destination is grassy and hilly, it can be determined that more calories will be easily burnt, the result of which is that the distance required for user to reach the destination can be quite short. Alternatively, an aggregated map can be created based on the similarity of the user to a select cohort in the crowdsourced data, based on, e.g., age and weight.

System Implementations

It is to be understood that embodiments of the present disclosure can be implemented in various forms of hardware, software, firmware, special purpose processes, or a combination thereof. In one embodiment, an embodiment of the present disclosure can be implemented in software as an application program tangible embodied on a computer readable program storage device. The application program can be uploaded to, and executed by, a machine comprising any suitable architecture. Furthermore, it is understood in advance that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed. An automatic troubleshooting system according to an embodiment of the disclosure is also suitable for a cloud implementation.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 5:
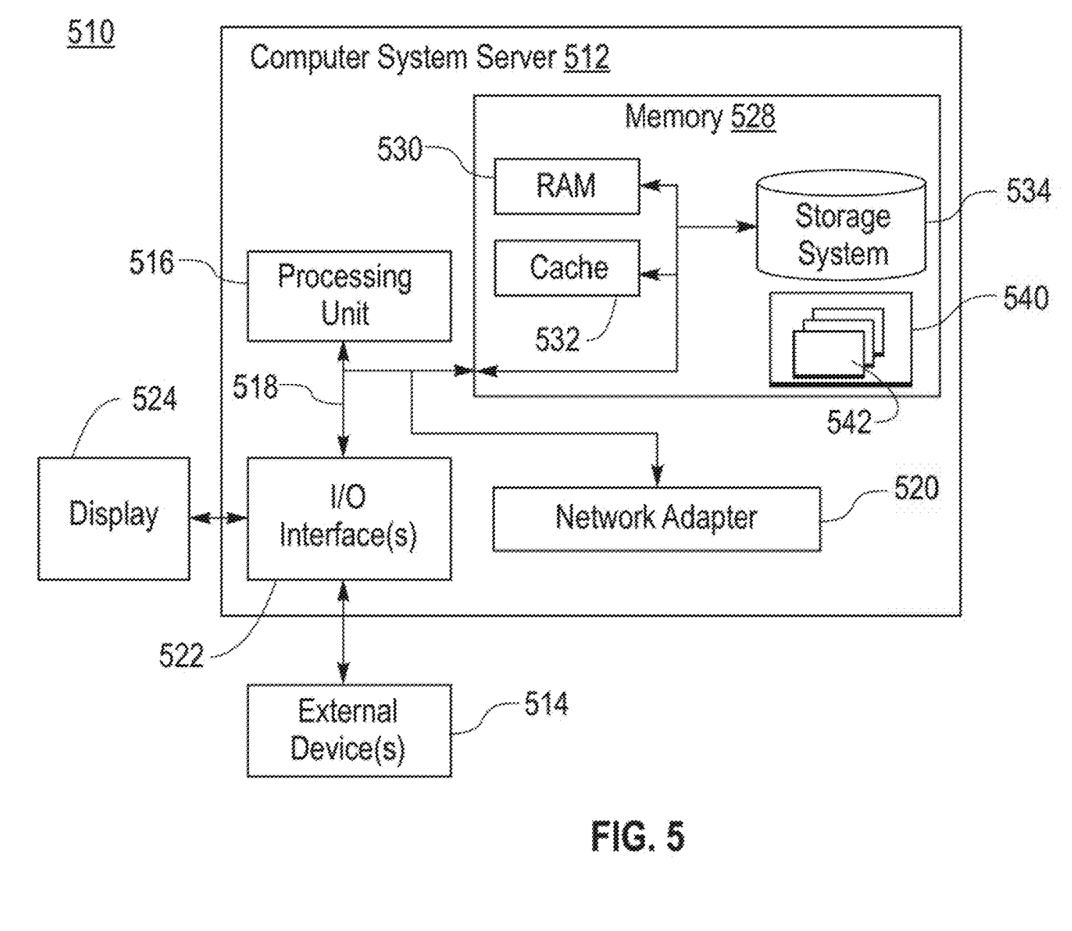
FIG. 5 is a schematic of an exemplary cloud computing node that implements an embodiment of the disclosure.

Referring now to FIG. 5, a schematic of an example of a cloud computing node is shown. Cloud computing node 510 is only one example of a suitable cloud computing node and is not intended to suggest any limitation as to the scope of use or functionality of embodiments of the disclosure described herein. Regardless, cloud computing node 510 is capable of being implemented and/or performing any of the functionality set forth hereinabove.

In cloud computing node 510 there is a computer system/server 512, which is operational with numerous other general purpose or special purpose computing system environments or configurations. Examples of well-known computing systems, environments, and/or configurations that may be suitable for use with computer system/server 512 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 512 may be described in the general context of computer system executable instructions, such as program modules, being executed by a computer system. Generally, program modules may include routines, programs, objects, components, logic, data structures, and so on that perform particular tasks or implement particular abstract data types. Computer system/server 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 512 in cloud computing node 510 is shown in the form of a general-purpose computing device. The components of computer system/server 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 512 typically includes a variety of computer system readable media. Such media may be any available media that is accessible by computer system/server 512, and it includes both volatile and non-volatile media, removable and non-removable media.

System memory 528 can include computer system readable media in the form of volatile memory, such as random access memory (RAM) 530 and/or cache memory 532. Computer system/server 512 may further include other removable/non-removable, volatile/non-volatile computer system storage media. By way of example only, storage system 534 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the disclosure.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the disclosure as described herein.

Computer system/server 512 may also communicate with one or more external devices 514 such as a keyboard, a pointing device, a display 524, etc.; one or more devices that enable a user to interact with computer system/server 512; and/or any devices (e.g., network card, modem, etc.) that enable computer system/server 512 to communicate with one or more other computing devices. Such communication can occur via Input/Output (I/O) interfaces 522. Still yet, computer system/server 512 can communicate with one or more networks such as a local area network (LAN), a general wide area network (WAN), and/or a public network (e.g., the Internet) via network adapter 520. As depicted, network adapter 520 communicates with the other components of computer system/server 512 via bus 518. It should be understood that although not shown, other hardware and/or software components could be used in conjunction with computer system/server 512. Examples, include, but are not limited to: microcode, device drivers, redundant processing units, external disk drive arrays, RAID systems, tape drives, and data archival storage systems, etc.

Figure 6:
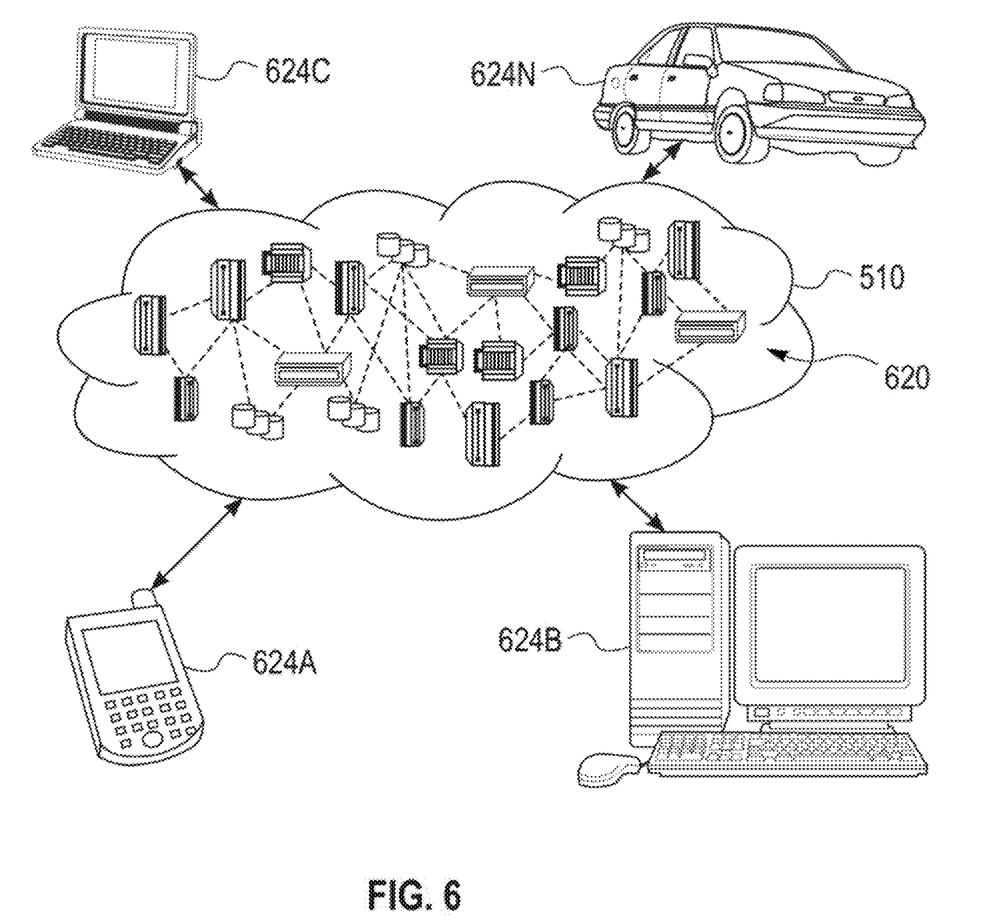
FIG. 6 shows an exemplary cloud computing environment according to embodiments of the disclosure.

Referring now to FIG. 6, illustrative cloud computing environment 620 is depicted. As shown, cloud computing environment 620 comprises one or more cloud computing nodes 510 with which local computing devices used by cloud consumers, such as, for example, personal digital assistant (PDA) or cellular telephone 624A, desktop computer 624B, laptop computer 624C, and/or automobile computer system 624N may communicate. Nodes 510 may communicate with one another. They may be grouped (not shown) physically or virtually, in one or more networks, such as Private, Community, Public, or Hybrid clouds as described hereinabove, or a combination thereof. This allows cloud computing environment 620 to offer infrastructure, platforms and/or software as services for which a cloud consumer does not need to maintain resources on a local computing device. It is understood that the types of computing devices 624A-N shown in FIG. 6 are intended to be illustrative only and that computing nodes 510 and cloud computing environment 620 can communicate with any type of computerized device over any type of network and/or network addressable connection (e.g., using a web browser).

While embodiments of the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. A computer-implemented method for determining routes, comprising the steps of:
receiving, by a server, users' location and health measures data, for a plurality of users;
analyzing, by the server, the plurality of users and their corresponding locations and health measures data to determine health behaviors of the plurality of users at a given location and time;
receiving, by the server, a request for a route from a mobile computing device of a requesting user, wherein the request includes the requesting user's location and health measures data;
normalizing, by the server, map regions without data for the requesting user with data for others of the plurality of users whose demographic data matches that of the requesting user and whose previous routes match the requesting user's route based on elevation, distance and pitch;
creating, by the server, an aggregated heatmap based on a select cohort of the plurality of users whose demographic data match that of the requesting user, wherein the heatmap shows various routes between the requesting user's location and destination;
developing, by the server, a route to the requesting user's destination from a current location to obtain a target health behavior within a given threshold or constraint based on the plurality of user's healthy behaviors; and
presenting, by the server, the route on the requesting user's mobile computing device.

2. The method of claim 1, further comprising joining the location and health measures data together into a single data element based on time.

3. The method of claim 1, wherein the health behaviors includes one or more of a number of calories, a number of steps, or at least a health measure.

4. The method of claim 1, wherein the route is presented as a map on the requesting user's mobile computing device.

5. The method of claim 1, wherein
location data includes a user's location based on GPS data or cell triangulation, a user's elevation, terrain, or environmental attributes,
health measures data include one or more of activity, blood pressure, speed, heartrate, or calories burned, and
said location and health measures data is stamped with a time and date.

6. The method of claim 1, wherein analyzing the plurality of users and their corresponding locations comprises aggregating biometric data and route data over a population of users in a data cloud for a given user and normalizing data over a distance for data values over a predetermined threshold.

7. The method of claim 6, further comprising creating an aggregated heatmap that represents health, geographical, and topographical data as part of the heatmap, and displaying the heatmap on the requesting user's mobile computing device.

8. The method of claim 1, wherein developing a route to the requesting user's destination comprises using a metric along with a graph traversal algorithm to select a route that increases health related values in the route assigned to a user.

9. The method of claim 8, wherein a metric includes one or more of a number of calories, a number of vertical steps, number of horizontal steps, increase in beats per minute, a distance, or mode of transportation.

10. The method of claim 1, further comprising presenting a variety of route options to the requesting user's mobile computing device, and receiving the requesting user's choice selected from the variety of route options.

11. The method of claim 1, further comprising creating a map that highlights opportunities to burn extra calories, and displaying the map on the requesting user's mobile computing device.

12. The method of claim 1, further comprising creating an aggregated heatmap that represents health, geographical, and topographical elements for the plurality of users, and displaying the heatmap on the requesting user's mobile computing device.

13. A non-transitory program storage device readable by a computer, tangibly embodying a program of instructions executed by the computer to perform the method steps for determining exercise routes, comprising the steps of:
receiving, by a server, users' location and health measures data, for a plurality of users;
analyzing, by the server, the plurality of users and their corresponding locations and health measures data to determine health behaviors of the plurality of users at a given location and time;
receiving, by the server, a request for a route from a mobile computing device of a requesting user, wherein the request includes the requesting user's location and health measures data;
normalizing, by the server, map regions without data for the requesting user with data for others of the plurality of users whose demographic data matches that of the requesting user and whose previous routes match the requesting user's route based on elevation, distance and pitch;
creating, by the server, an aggregated heatmap based on a select cohort of the plurality of users whose demographic data match that of the requesting user, wherein the heatmap shows a plurality of routes between the requesting user's location and destination;
developing, by the server, a route to the requesting user's destination from a current location to obtain a target health behavior within a given threshold or constraint based on the plurality of user's healthy behaviors; and
presenting, by the server, the route on the requesting user's mobile computing device.

14. The computer readable program storage device of claim 13, further comprising joining the location and health measures data together into a single data element based on time.

15. The computer readable program storage device of claim 13, wherein the health behaviors includes one or more of a number of calories, a number of steps, or at least a health measure.

16. The computer readable program storage device of claim 13, wherein the route is presented as a map on the requesting user's mobile computing device.

17. The computer readable program storage device of claim 13, location data includes a user's location based on GPS data or cell triangulation, a user's elevation, terrain, or environmental attributes,
health measures data include one or more of activity, blood pressure, speed, heartrate, or calories burned, and said location and health measures data is stamped with a time and date.

18. The computer readable program storage device of claim 13, wherein analyzing the plurality of users and their corresponding locations data comprises aggregating biometric data and route data over a population of users in a data cloud for a given user and normalizing data over a distance for data values over a predetermined threshold.

19. The computer readable program storage device of claim 18, the method further comprising creating an aggregated heatmap that represents health, geographical, and topographical data as part of the heatmap, and displaying the heatmap on the requesting user's mobile computing device.

20. The computer readable program storage device of claim 13, wherein developing a route to the requesting user's destination comprises using a metric along with a graph traversal algorithm to select a route that increases health related values in the route assigned to a user.

21. The computer readable program storage device of claim 20, wherein a metric includes one or more of a number of calories, a number of vertical steps, number of horizontal steps, increase in beats per minute, a distance, or mode of transportation.

22. The computer readable program storage device of claim 13, the method further comprising presenting a variety of route options to the requesting user's mobile computing device, and receiving the requesting user's choice selected from the variety of route options.

23. The computer readable program storage device of claim 13, the method further comprising creating a map that highlights opportunities to burn extra calories, and displaying the map on the requesting user's mobile computing device.

24. The computer readable program storage device of claim 13, the method further comprising creating an aggregated heatmap that represents health, geographical, and topographical elements for the plurality of users, and displaying the heatmap on the requesting user's mobile computing device.

25. The method of claim 1, wherein the requesting user explicitly includes the requesting user's location and health measures data in the request.

26. The method of claim 1, wherein the requesting user's location and health measures data are obtained from the requesting user's mobile computing device.

27. The computer readable program storage device of claim 13, wherein the requesting user explicitly includes the requesting user's location and health measures data in the request.

28. The computer readable program storage device of claim 13, wherein the requesting user's location and health measures data are obtained from the requesting user's mobile computing device.

* * * * *